United States Patent [19]

Chan et al.

[11] Patent Number: 5,721,095
[45] Date of Patent: Feb. 24, 1998

[54] HIV-1/HIV-2 VIRAL DETECTION KIT AND METHOD

[75] Inventors: Lily Chan, Singapore; Yoke Wah Sum, Jurong Town; May Fong Yin; Lee Fang Lim, both of Singapore, all of Singapore

[73] Assignee: Genelabs Diagnostics Pte Ltd., Singapore, Singapore

[21] Appl. No.: 486,837

[22] Filed: Jun. 7, 1995

Related U.S. Application Data

[63] Continuation of Ser. No. 285,880, Aug. 4, 1994, which is a continuation of Ser. No. 68,618, May 26, 1993, which is a continuation of Ser. No. 912,220, Jul. 10, 1992, which is a continuation of Ser. No. 568,144, Aug. 16, 1990.

[51] Int. Cl.$^6$ .......................... C12Q 1/70; G01N 33/564; G01N 33/53; G01N 33/544
[52] U.S. Cl. .......................... 435/5; 435/970; 435/974; 436/530; 436/543
[58] Field of Search .................. 435/5, 970, 974; 436/530, 543

[56] References Cited

U.S. PATENT DOCUMENTS

| 4,452,901 | 6/1984 | Gordon et al. | 436/506 |
|---|---|---|---|
| 4,520,113 | 5/1985 | Gallo et al. | 436/504 |
| 4,629,783 | 12/1986 | Cosand | 435/5 |
| 4,735,896 | 4/1988 | Wang et al. | 435/5 |
| 4,918,000 | 4/1990 | Schubert | 435/7 |

FOREIGN PATENT DOCUMENTS

| 2009198 | 2/1990 | Canada . |
|---|---|---|
| 85307260 | 10/1985 | European Pat. Off. . |
| 87100064 | 1/1987 | European Pat. Off. . |
| WO89/00609 | 1/1989 | WIPO . |
| WO89/01158 | 2/1989 | WIPO . |
| WO89/01527 | 2/1989 | WIPO . |

OTHER PUBLICATIONS

Vander Poel, et al., "Diagnosis and Prevalence of HIV-2 Antibodies in Different Population Subsets in the Netherlands," *Fox Sang*, vol. 57, pp. 249–253, 1989.
Dagani, "The Problem of Diagnostic Tests," *C&EN*, pp. 35–40, Nov. 23, 1987.
Schmidt, et al., "Densitometric Analysis of Western Blot (Immunoblot) Assays for Human Immunodeficiency Virus Antibodies and Correlation with Clinical Status", *J. Clin. Microbiol.*, vol. 25, pp. 1993–1998, 1987.
Gnann, et al., "Synthetic Peptide Immunoassay Distinguishes HIV Type 1 and HIV Type 2 Infections", *Science*, vol. 237, pp. 1346–1349, 1987.
Caruson, et al., "Rapid Discrimination Between HIV-1 and HIV-2 Infection", *The Lancet*, pp. 1156–1157, Nov. 11, 1989.
Crowl, R., et al., "HTLV-III env Gene Products Synthesized in *E. coli* are Recognized by Antibodies Present in the Sera of AIDS Patients," *Cell* 41:979–986 (1985).
Dagani, R., "The Problem of Diagnostic Tests," *Chem. & Engr. News* 65(47):34–40 (1987).
deClercq, E., "Targets and Strategies for the Antiviral Chemotherapy of AIDS," *TIPS* 11:198 (1990).
Franchini, G., et al., "Sequence of Simian Immunodeficiency Virus and its Relationship to the Human Immodeficiency Viruses," *Nature* 328:539 (1987).
Gnann, J.W., Jr., et al., "Synthetic Peptide Immunoassay Distinguishes HIV Type 1 and HIV Type 2 Infections," *Science* 237:1346 (1987).
Guyader, Mireille, et al., "Genome Organization of Human Immunodeficiency Virus Type 2," *Nature* 326:662–669 (1987).
Hawkes, et al., "A Dot-Immunobinding Assay for Monoclonal and Other Antibodies," *Anal. Biochem.* 119:142–147 (1982).
Holzer, T.J., et al., "Discrimination of HIV–2 Infection from HIV–1 Infection by Western Blot and Radioimmununoprecipitation Analysis," *AIDS Res. and Human Retroviruses* 6(4):515 (1990).
Hunt, J.C., et al., "Discrimination Betwen HIV–1 and HIV–2–Sero–positive Individuals Using Mouse Monoclonal Antibodies Directed to HIV Transmembrane Proteins," *AIDS Res. and Human Retroviruses* 6(7):883 (1990).
INNO–LIA HIV–1/HIV–2 AB Advertisement, *AIDS* 5(3):backcover (1989).
Ng, V.L., et al., "Reliable Confirmation of Antibodies to Human Immunodeficiency Virus Type 1 (HIV–1) with an Enzyme–Linked Immuno–assay Using Recombinant Antigens Derived from the HIV–1 *gag, pol* and *env* Genes," *J. Clin. Microbiol.* 27(5):977–982 (1989).
Norrby, E., et al., "Discrimination Between Antibodies to HIV and to Related Retroviruses Using Site–Directed Serology," *Nature* 329:248 (1987).
Petteway, S.R., Jr., et al., "Immunological Characterization of HTLV–III Recombinant Proteins: Potential ad Diagnostics and Vaccine Candidates," *Viruses and Human Cancer*, pp. 15–28 (1987).
Popovic, M., et al., "Detection, Isolation, and Continuous Production of Cytopathic Retroviruses (HTLV–III) from Patients with AIDS and pre–AIDS," *Science* 224:506–508 (1984).
Rey, Marie–Anne, et al., "Characterization of Human Immunodeficiency Virus Type 2 Envelope Glycoproteins Dimerization of the Glycoprotein Precursor During Processing," *J. Virol.* 63(2):647–658 (1989).

(List continued on next page.)

*Primary Examiner*—Michael P. Woodward
*Assistant Examiner*—Brenda Brumback
*Attorney, Agent, or Firm*—Dehlinger & Associates

[57] ABSTRACT

A method for producing an improved solid phase antigenic reagent useful in an immunoassay for detecting antibodies specific for a virus, such as the human immunodeficiency virus, is disclosed which comprises the addition to a natural viral lysate a synthetic or recombinant viral protein or peptide. Also provided is an improved immunoassay utilizing the solid phase antigenic reagent.

6 Claims, 5 Drawing Sheets

OTHER PUBLICATIONS

Samuel, K.P., et al., "High–Level Bacterial Expression and Purification of Human T–Lymphotropic Virus Type I (HTLV–I) Transmembrane *env* Protein," *Gene Anal. Techn.* 2:60–66 (1985).

Samuel, K.P., et al., "Bacterial and Characterization of Nine Polypeptides Encoded by Segments of the Envelope Gene of Human Immunodeficiency Virus," *Gene* 64:121–134 (1988).

Towbin, H., et al., "Electrophoretic Transfer of Proteins from Polyacrylamide Gels to Nitrocellulose Sheets: Procedure and Some Applications," *Proc. Natl. Acad. Sci. U.S.A.* 76(9):4350–4354 (1979).

Tsang, V.C.W., et al., "Enzyme–Linked Immunoelectrotransfer Blot Techniques (EITP) for Studying the Specificities of Antigens and Antibodies Separated by Gel Electrophoresis," *Methods in Enzymol.* 92:377 (1983).

**IMMUNOBLOT OF
HIV-1 VIRAL LYSATE
ANTIGEN**

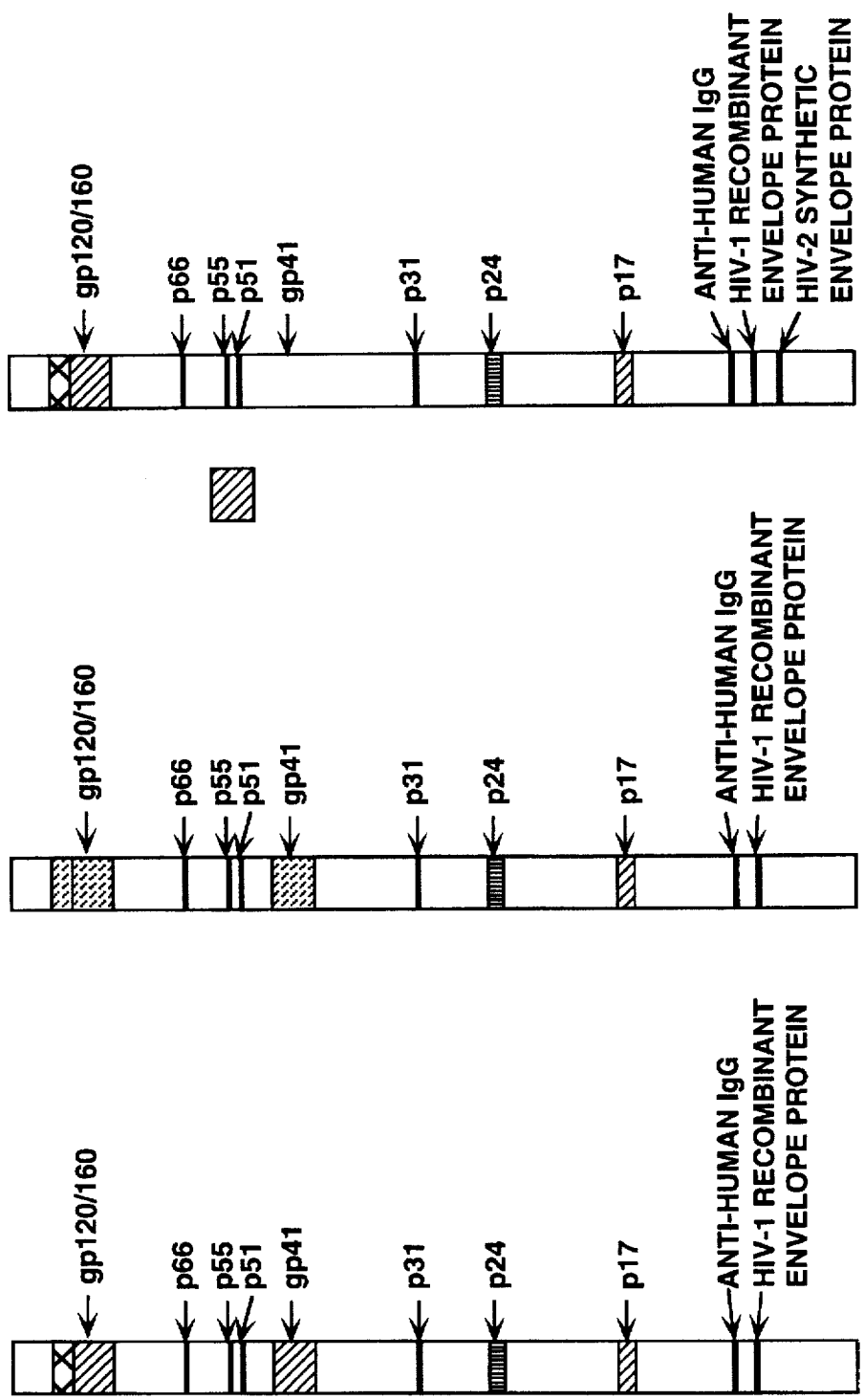

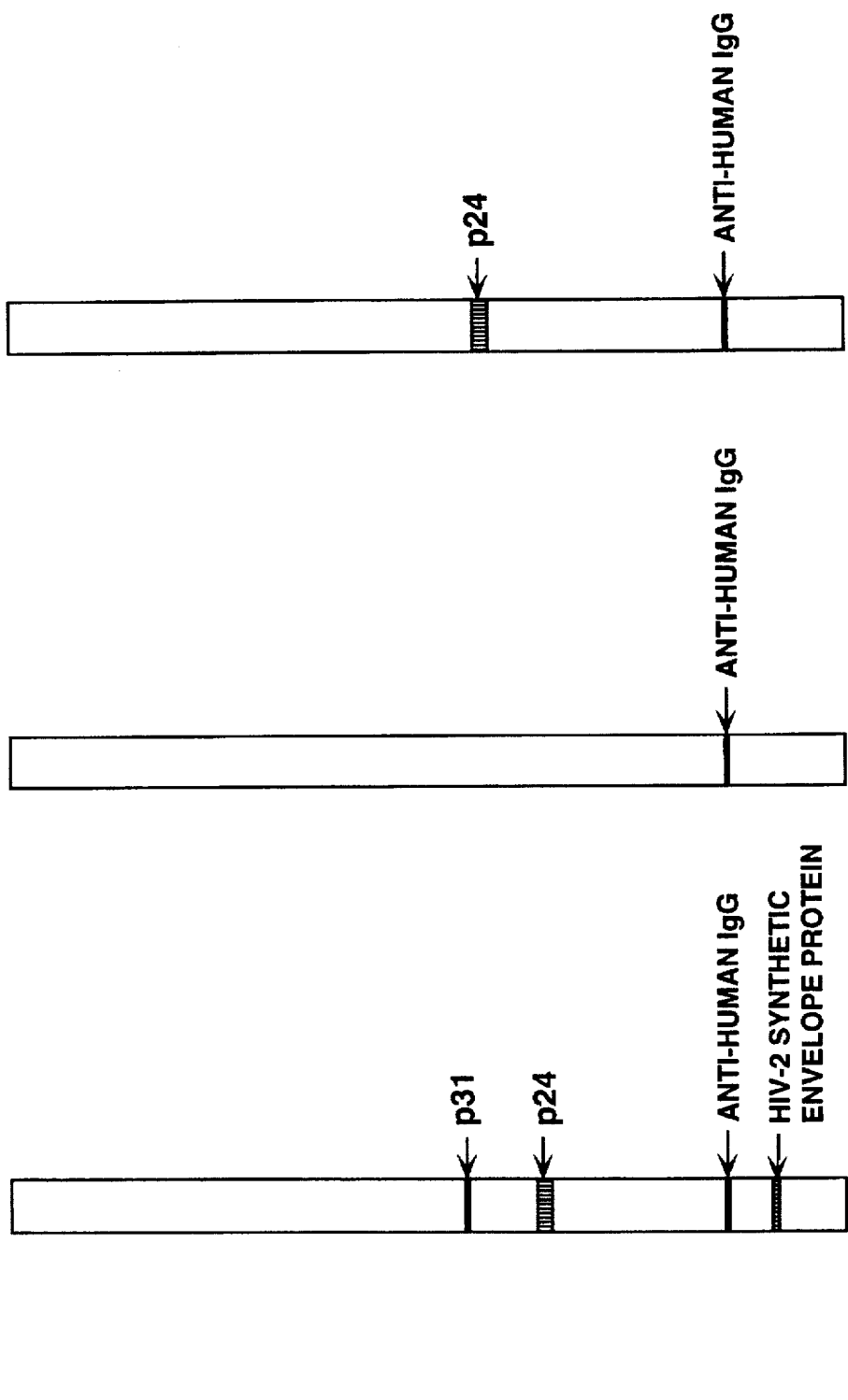

IMMUNOBLOT SHOWING
SEROREACTIVITY TO
HIV-1 INFECTION

IMMUNOBLOT SHOWING
SEROREACTIVITY TO
HIV-1 INFECTION

IMMUNOBLOT SHOWING SEROREACTIVITY TO HIV-1/HTLV-1 INFECTION

HIV-1/HIV-2 VIRAL DETECTION KIT AND METHOD

This application is a continuation of U.S. patent application Ser. No. 08/285,880, filed Aug. 4, 1994, herein incorporated by reference, which is a continuation of U.S. patent application Ser. No. 08/068,618, filed May 26, 1993, which is a continuation of U.S. patent application Ser. No. 07/912,220, filed Jul. 10, 1992, which is a continuation of U.S. patent application Ser. No. 07/568,144, filed Aug. 16, 1990.

BACKGROUND OF THE INVENTION

1. Field of the Invention

The invention relates to a test designed to detect antibodies to human retroviral infections, more specifically the Human Immunodeficiency Virus type 1 (HIV-1) and type 2 (HIV-2), the etiologic agents of Acquired Immunodeficiency Syndrome (AIDS).

2. Information Disclosure Statement

Laboratory tests currently used to detect HIV infection are based on the observation that individuals infected with HIV will develop virus-specific antibodies within a few weeks, or months at the latest. Serological diagnosis of HIV infection rests on the detection of a host immune response to viral antigens encoded by the 3 major viral structural genes. The gag gene encodes the major viral core proteins, p17 (molecular weight 17 kD), p24 (molecular weight 24 kD) and their precursor, p55 (molecular weight 55 kD). The env gene encodes the envelope glycoprotein precursor, gp160 (molecular weight 160 kD) which is cleaved into an external envelope domain, gp120 (molecular weight 120 kD), and the transmembrane region, gp41 (molecular weight, 41 kD). The pol gene encodes major proteins, such as reverse transcriptase p66 and p51 (molecular weights 66 and 51 kD, respectively) and a p31 endonuclease (molecular weight 31 kD) component. Several other viral proteins, mainly having regulatory functions, are encoded and expressed by the HIV genome, but none of these gene products are sufficiently immunogenic to be used at routine markers for serological diagnosis.

Several methods for the detection of antibodies to HIV-1 have been developed over the years, and, as the epidemic continues to spread, it becomes important that diagnostic methods have the capability to accurately identify infected individuals.

Enzyme-linked immunoassays (ELISAs) are widely used to screen for presence of virus-specific antibodies (Groopman, J. E. et al., *J. Infec. Dis.* 153:736–742 (1986); Centers for Disease Control, "Update: Serologic testing for antibody to Human Immunodeficiency virus," *MMWR* 36:833–840, 845 (1988)). Such a test format can be extremely sensitive but carries with it a potential for being less specific, leading to false positive reactions. Supplementary tests that are more specific are commonly used. A positive HIV-1 serological diagnosis has significant psychosocial implications for the individual being diagnosed. It is all the more pressing, therefore, that test results be accurate and reliable. Furthermore, although users of HIV immunoblot confirmatory assays may appreciate the inherent limitations in assays using only purified natural viral antigens, they have become comfortable with the reactivity profiles obtained in such assays and may thus be hesitant to change. Supplementary tests offering greater specificity and sensitivity than a standard ELISA include the western blot test, indirect immunofluorescence and radioimmunoprecipitation assays (*MMWR*, 1988, supra). Among these supplementary tests, the western blot is most informative and is the current "gold standard" for serological confirmation of HIV infections ("Interpretation and use of the Western Blot Assay for serodiagnosis of HIV-1 Infections," *MMWR* 38, No. S-7 (1989)).

In the Western Blot, HIV-1 virus is harvested from tissue culture, lysed, and the individual viral proteins separated by polyacrylamide gel electrophoresis (PAGE). The separated proteins are then transferred to nitrocellulose membranes by electroblotting ("immunoblot strips"). A test serum is incubated with the immunoblot strips and HIV-antibodies, if present, bind to the separated viral proteins. The strips are washed to remove excess unbound proteins, and presence of the specific antibodies is visualized by incubation with enzyme-conjugated anti-human immunoglobulin antibodies and chromogenic substrates. Thus, the presence of an antibody in sufficient concentration results in the staining of the characteristic viral protein "band."

Over the past five years, laboratories and health organizations have delineated several criteria required for determining that a HIV-1 western blot profile is positive. Qualitative assessment of results based on the number of stained bands and the particular band patterns, has indicated that samples obtained early in infection, or infection by some cross-reacting viruses, may yield "atypical" blot patterns. Such atypical patterns are generally considered "Indeterminate" with regard to diagnostic criteria of positivity. In such circumstances, a follow-up evaluation of the individual is usually performed.

Attempts have been made to improve the reliability of western blot analysis by (a) removing subjectivity in interpretation, and (b) standardization of the reagents used in manufacturing. However, the configuration of the test format as currently practiced is subject to a variety of complicating factors. For example, the relative concentrations of the viral proteins from a particular tissue culture preparation will vary, and this variability is reflected in the material used in manufacture of the test.

These problems prompted attempts at improvement by using viral antigens from synthetic sources (Crowl, R. et al., 1985. *Cell* 41: 979–986 (1985); Samuel, K. P. et al., *Gene* 64: 121–134 (1988)). Several structural and nonstructural HIV gene sequences have been cloned and their proteins expressed. Immunogenic epitopes from such regions have also been identified and synthesized. Mostly, these antigens have been used in the ELISA format for screening test purposes. In some instances these antigens have been directly applied onto nitrocellulose sheets and evaluated for use as a replacement for the conventional western blot. Such test formats also have certain limitations.

Molecularly cloned antigens, or synthetic peptides may be limited in the "repertoire" of epitopes presented, thus restricting the sensitivity and range of detection of seroreactivity of an extensive array of antibody responses.

A major deficiency in the art is therefore the absence of a single confirmatory immunoblot assay method that provides not only the well-characterized natural antigen reactivity profile, but also has the capability of increased sensitivity and immediate qualitative differentiation of infection by viral subtypes, such as HIV-1 and HIV-2.

SUMMARY OF THE INVENTION

It is an object of the present invention to overcome the deficiencies in the work discussed above.

It is a further object of the invention to provide an immunoblot format and immunoassay with significantly improved sensitivity and specificity for the serological diagnosis of viral infection, especially with human immunodeficiency virus (HIV-1, HIV-2).

It is a further object of the invention to provide an immunoassay format with significantly improved specificity for serologically distinguishing HIV-1 from HIV-2 infection.

This invention is further directed to an extension of such an immunoassay format for serologically distinguishing viral infections other than HIV-1 and HIV-2, such as HTLV-I and HTLV-II, to enhance sensitivity and specificity of detecting a particular viral infection by serodiagnosis.

Specifically, this invention relates to a new and enhanced method for the detection of antibodies to a virus, in particular Human Immunodeficiency Virus type 1 (HIV-1) and/or type 2 (HIV-2) by use of an augmented western blot format and assay. The invention is directed to an improved immunoassay for the detection of antibodies specific for a virus in a biological fluid comprising:

(a) providing a solid phase support containing electrophoretically separated natural viral proteins and additionally having bound thereto at least one synthetic viral protein or peptide;

(b) contacting the biological fluid with the solid phase support allowing an antibody in the biological fluid to bind to the natural or synthetic protein forming an antigen-antibody complex;

(c) contacting the antigen-antibody complex with a detectably labelled binding partner capable of binding to the antibody; and (d) detecting the detectable label on the solid phase support as a measure of the presence of the antibody in the fluid.

The invention is also directed to a method for producing an improved immunoblot format useful in an immunoassay for detecting antibodies specific for a virus, comprising the steps of:

(a) applying a preparation of natural proteins of the virus derived from tissue culture to a polyacrylamide gel;

(b) electrophoretically separating the viral proteins;

(c) transferring the separated proteins to a solid phase support; and (d) directly applying to the solid phase support at least one synthetic viral protein at a site not occupied by the transferred proteins, using the technique of stamping, imprinting, line drawing or slotting with a manifold apparatus.

The above method may also include directly applying to the solid support a human anti-immunoglobulin antibody to serve as a positive control by the technique of stamping, imprinting, line drawing, or slotting with a manifold apparatus, at a site not occupied by the transferred proteins or the directly applied synthetic viral protein.

The invention further provides a method for producing an improved immunoblot format useful in an immunoassay for detecting antibodies specific for a virus, comprising the steps of:

(a) applying a mixture of a preparation of natural proteins of the virus derived from tissue culture and at least one synthetic viral protein to a polyacrylamide gel;

(b) electrophoretically separating the natural and synthetic viral proteins; and (c) transferring the separated proteins to a solid phase support.

The new method and assay of the present invention, based on augmenting the natural protein western blot with synthetic proteins from the same virus (or a different virus) provide a distinctly sensitive and specific detection device. Additionally use of this method of detection will provide a more complete serological profile.

BRIEF DESCRIPTION OF THE DRAWINGS

FIG. 2 presents immunoblot profiles of the augmented immunoblot process format as described in Example 1 with sera from individuals infected with HIV-1, HIV-2, dual HIV-1/HIV-2, and non-infected individuals, as well as a sample of serum which is reactive only to gag proteins: (a) Serum with HIV-1 reactivity shows reactivity to the typical HIV-1 viral antigen profile and to the augmented recombinant envelope band confirming HIV-1 infection; (b) Serum with HIV-1 reactivity but having weak to no reactivity with natural envelope proteins due to insufficient natural envelope proteins on the immunoblot strip; augmentation with recombinant envelope protein allows immediate confirmation of envelope reactivity; (c) Serum with dual HIV-1/HIV-2 reactivity is shown as immediately distinguishable from serum from an individual with a single infection; (d) Serum with HIV-2 reactivity shows reactivity with the augmented HIV-2 envelope band which immediately distinguishes HIV-2 from HIV-1 infection; (e) A nonreactive sera shows reactivity only to the anti-human IgG, indicating presence of a serum sample in the assay; this serves as a positive control for the assay ensuring that results are not read as a false negative; (f) Immunoblot profile of a serum which is gag-reactive only.

DESCRIPTION OF THE PREFERRED EMBODIMENTS

Figure 1:
FIG. 1 presents an immunoblot showing a typical HIV-1 viral antigen profile observed with the conventional western blot assay with HIV-1 reactive serum.
Figure 3A:
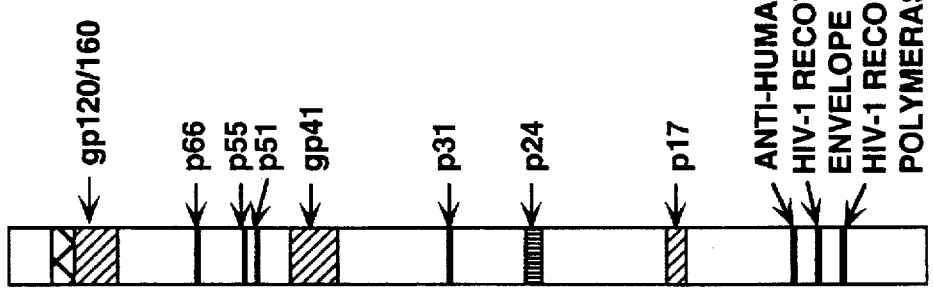
FIG. 3 illustrates immunoblot profiles of the augmented assay format wherein the strip is augmented with synthetic polymerase protein (a) and synthetic core protein (b).
Figure 3B:
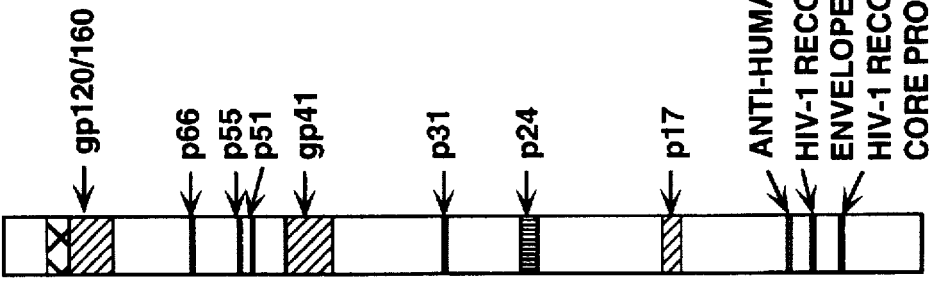
Figure 4:
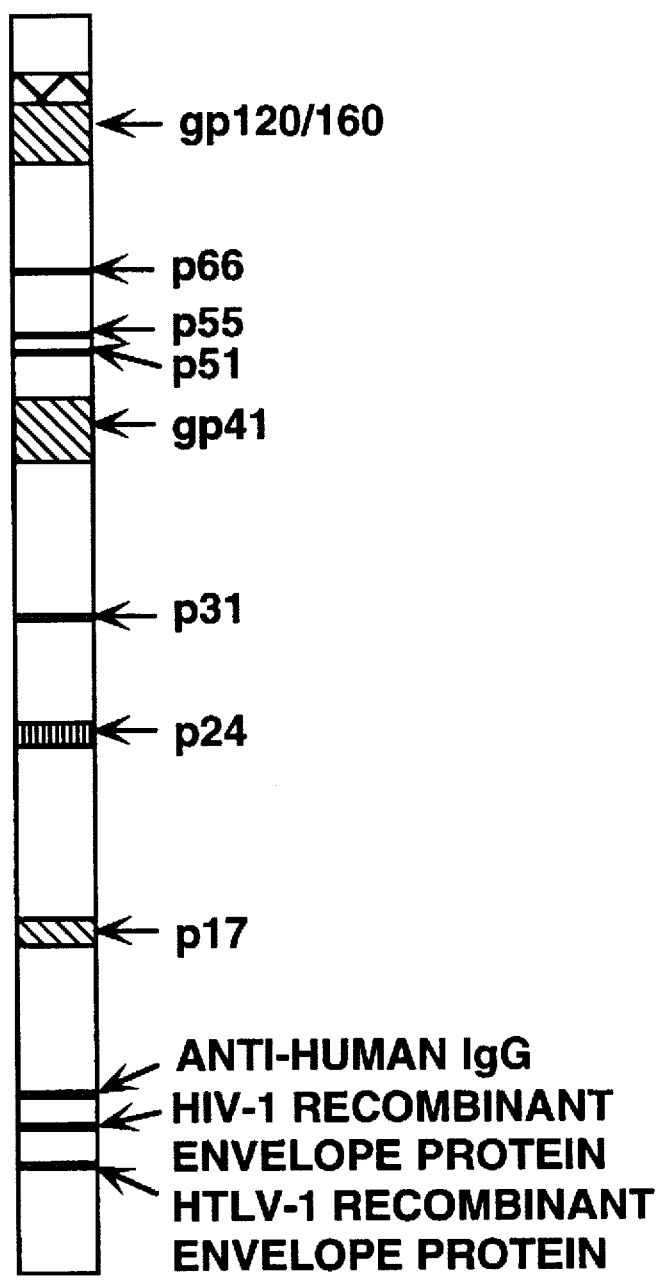
FIG. 4 illustrates an immunoblot profile of the augmented assay format wherein the strip is augmented with a synthetic HTLV-I envelope protein.

The present invention involves three basic procedures. In the first, viral proteins, preferably retroviral proteins of the retroviruses, HIV-1 or HIV-2, are prepared from lysates of virus obtained from tissue culture, and are separated by western blot, using PAGE followed by blotting onto a solid phase support, such as nitrocellulose.

In the second procedure, genetically engineered or chemically synthesized viral proteins or peptides are directly applied to the same solid support, in order to augment the profile of the electrophoretically transferred proteins. Viral protein or peptide antigens produced either by recombinant or synthetic means will be referred to herein collectively as "synthetic."

In the third procedure, an immunoassay is carried out to detect the presence of antibodies in a biological fluid, such as the serum, of virus-infected individuals to the transblotted as well as to the directly applied proteins.

By the term "biological fluid" is intended any fluid derived from the body of a normal or diseased subject, such as blood, serum, plasma, lymph, urine, Saliva, tears, cerebrospinal fluid, milk, amniotic fluid, bile, ascites fluid, pus and the like. Also included within the meaning of this term as used herein is a tissue extract, or the culture fluid in which any cells or tissue preparation from the subject has been incubated.

HIV-1 virus particles are harvested from the supernatants of virus-infected cell lines and concentrated and purified via a sucrose density gradient using methods well-known in the art. The virions are lysed and inactivated using a detergent, such as NP40. The method of Popovic et al. (*Science* 224:497–500 (1984)) is preferred. The antigens contained in the viral lysate are separated by electrophoresis on a polyacrylamide slab gel in the presence of sodium dodecyl sulfate. The electrophoresed proteins are transferred to a solid phase support using methods known in the art. (See: Towbin H, et al., *Proc Natl Acad. Sci. USA* 76: 4350 (1979); Tsang, V. C. W. et al., *Methods in Enzymology* 92:377–391 (1983), which references are hereby incorporated by reference).

The solid phase support useful for the methods of the present invention is preferably nitrocellulose. Alternatively, other solid phase supports may be used, including, but not limited to, nylon, charge modified nylon, diazobenzyloxymethyl paper, and the like.

The next phase of the process according to the invention is the application of the synthetic proteins or peptides directly to the solid phase support. The synthetic proteins or peptides can be chemically synthesized or produced by recombinant techniques in prokaryotic cells, preferably bacteria, or in eukaryotic cells such as yeast cells or mammalian cells.

Synthetic protein or peptide antigens known to be antigenic in the species being tested for viral antibodies, preferably humans, are generally useful in the present invention. The preferred viral antigens are those known to be valuable for diagnostic purposes.

The HIV-1 proteins used to augment the immunoblot of the present invention may be purified proteins from the natural virus preparation, recombinant proteins and peptides, or functional derivatives thereof. Such purified or recombinant proteins of HIV may be the entire, or a portion of the gp120/160 envelope glycoprotein, gp41, p66, p31, or p24. Better defined viral protein antigens in the form of peptides, such as a p24 epitope that does not cross-react with normal human serum, are also contemplated within the scope of the invention.

In one embodiment, the HIV-1 recombinant envelope protein encoded by the plasmid p-env 9 is used (Petteway, S. R. et al., *UCLA SYMP. ON MOL. CELL. BIOL.*, "Viruses and Human Cancer," 43:15–28 (1987)). In a preferred embodiment, the HIV envelope peptide having the sequence RILAVERYLKDQQLLGIWGCSGK, a variation of the UBI peptide is used. In another embodiment, the peptide encoded by clone 566 (Samuel, K. P. et al., *Gene* 64:121–134 (1988)) is used.

For the HIV-2 specific protein, the peptide sequence LNSWGCAFRQVCHTTVPW, which is a modification of the peptide disclosed in McCormick et al. (*Science* 237:1346–1349 (1987)), is preferred.

For HTLV-I specific proteins, an envelope recombinant, gp21 (Samuel, K. P. et al., *Gene Anal. Techn.* 2:60–66 (1985)) is preferred. By "functional derivative" is meant a "fragment," "variant," "analog," or "chemical derivative" of a viral protein, which terms are defined below. A functional derivative retains at least a portion of the function of the viral protein which permits its utility in accordance with the present invention, that is, its recognition by and binding to an antibody.

A "fragment" of a viral protein refers to any subset of the molecule, that is, a shorter peptide.

A "variant" of a viral protein refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity.

An "analog" of a viral protein refers to a non-natural molecule substantially similar to either the entire molecule or a fragment thereof.

A "chemical derivative" of a viral protein contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

The viral protein or peptide is directly applied onto the solid phase support to augment the serum reactivity profile provided by antigens of the natural viral lysate.

For reproducible sensitive western blot profiles, it is desirable that all individual viral proteins be present in approximately equal concentrations. It is rare that viral antigens in lysates of virions from tissue culture provide such uniformity in lot to lot harvests. Also, the electrophoretic transfer of the natural viral proteins separated by SDS-PAGE may result in non-random selective retention of different viral proteins based on molecular weight versus transblot time. Lower molecular weight proteins tend to transfer more rapidly from the gel to the nitrocellulose. Commonly, viral glycoproteins are transferred inefficiently due both to their chemical nature as well as molecular weight. Therefore augmentation of the immunoblot profile of natural viral antigens with synthetic viral protein or peptide antigens provides several advantages.

The antigens can be made available reproducibly and uniformly, decreasing the lot-to-lot variability of the immunoblots. Immunogenic viral proteins which are inherently present in lower concentration, such as envelope glycoproteins or gag proteins, like p24, can be applied directly onto the solid phase support to improve the sensitivity and specificity of the test.

Viral proteins or peptides specific to viruses other than HIV-1, such as, for example, HIV-2, HTLV-I, HTLV-II, hepatitis virus, Epstein-Bart Virus, Herpes Simplex Virus 1 and 2, and the like, can also be applied to the solid support. Presence of such viral antigens will allow immediate serological detection and distinction of viral infections.

The synthetic proteins or peptides may be applied to the solid phase support by any one of several known procedures. If the molecular weight of the synthetic viral protein or peptide is such that it is within the range of molecular weights of the natural viral proteins, and further, if it will be electrophoretically distinct, such a protein or peptide can be mixed with the natural viral lysate prior to electrophoresis and transblotting (Towbin H, et al., supra; Tsang, V. C. W. et al., supra).

However, genetically engineered proteins may occur as aggregates or in more than one form dependent on the nucleotide sequences inserted into the expression vectors. In such cases, as well as in the case of low molecular weight synthetic peptides, it is preferable that these proteins be directly applied via a slot or dot blotting procedure which are well known in the art. Other procedures like stamping, or line drawing, also known in the art, can be used. (See, for example, Linnecke, U.S. Pat. No. 4,748,042).

In a preferred embodiment of the present invention, three proteins are used to augment the western blot: anti human IgG antibody or human IgG, a genetically engineered HIV-1 envelope protein and synthetic peptide corresponding to a portion of a HIV-2 envelope protein. More preferably, an HIV-1 envelope peptide, RILAVERYLKDQQLLGIWGCSGK, is used in place of the envelope protein. A preferred means of applying the augmenting proteins or peptides to the immunoblot is by slotting on to the nitrocellulose after the natural viral proteins have been electrophoresed and transblotted.

Anti-human IgG or human IgG is applied directly onto the membrane to provide within-assay quality control. Thus the addition of sera and conjugate, respectively, will be indicated by color development of this band on the nitrocellulose after the performance of the immunoassay. This will obviate the possibility of a false negative result due to the possibility that a test serum sample was inadvertently left off. Whenever a human serum sample is added, the anti-human IgG will react with it and the band in the appropriate location will be detected. A sample lacking any anti-viral antibody (seronegative) will have no reactivity to any viral bands but will be positive for the anti-human IgG band. Absence of a colored band where the anti-human IgG band is located is an indication that a serum sample was not added in the immunoassay.

In the preferred slotting procedure, the transblotted nitrocellulose containing the electrophoresed natural viral antigens is placed onto a slotting manifold. The manifold is constructed such that each slot provides a band preferably not more than 1.5 mm wide and 13 cm in length. Slotting is preferably performed on areas on the transblotted nitrocellulose not occupied by the transblotted viral proteins. In a preferred embodiment, the slotted bands are 1.5 mm apart and the proteins are slotted 1 to 1.5 mm from the lower end of the zone occupied by the transblotted natural viral proteins. Slotting can be performed immediately after the transblot of the natural viral antigens. Alternatively, the transblotted nitrocellulose can be dried, kept in a dry container until ready for slotting at another time. The amounts of synthetic proteins slotted are predetermined via a series of sensitivity and specificity titrations, known to one of skill in the art. The proteins are diluted preferably in 0.1M carbonate buffer, pH 9.6, applied into the slots using a micropipettor or syringe. A 1 ml syringe is preferred.

The slotting apparatus is a modification of a slotting dot manifold equipment available commercially from companies like BIO-RAD (Richmond, Calif.) or Life Sciences, Inc. (Gaithersburg, Md.). The solid phase support, preferably nitrocellulose, to be slotted is held in place via clamps or screws. After addition of the protein or peptide, excess material is removed from the slots via aspiration through the slots attached to a vacuum pump.

In addition to slotting, the proteins can be applied by stamping, line drawing, or dot blotting.

The solid phase support is removed and blocked in a buffer containing a detergent and blotting proteins. Nonfat dry milk is a preferred blocking agent although any protein-containing blocking agent known in the art can be used. The solid phase support is dried and cut into 3 or 4 mm-wide strips and stored in desiccated dry containers until ready for use.

The presence or absence of antibodies to the viral antigens is detected via an immunoassay procedure. This can be performed following previously established procedures well known in the art. The serum sample to be tested is diluted in the presence of a Tris-based buffer containing blocking proteins, such as non-fat dry milk. The diluted serum sample is incubated with the augmented viral antigen strip prepared as described above. Antibodies to HIV-1 will bind to antigens located on the strip as discrete bands. The strips are then washed to remove unbound material. Visualization of the antibodies specifically bound to the viral antigens is accomplished in situ using a species-specific second antibody specific for the immunoglobulin comprising the anti-HIV antibody, such as goat anti-human IgG. Alternatively, a ligand which will bind specifically to the human antibody, such as Staphylococcal protein A, is used.

Once the secondary binding reagent is chosen, the appropriate detection reagent can be selected. Useful detection reagents for the present invention include enzymes, preferably alkaline phosphatase (AP), or horseradish peroxidase (HRP). Other enzymes which can be used include, but are not limited to, malate dehydrogenase, staphylococcal nuclease, delta-V-steroid isomerase, yeast alcohol dehydrogenase, alpha-glycerophosphate dehydrogenase, triose phosphate isomerase, asparaginase, glucose oxidase, beta-galactosidase, ribonuclease, urease, catalase, glucose-6-phosphate dehydrogenase, glucoamylase and acetylcholinesterase.

In another embodiment, colloidal gold spheres rather than enzymes are used as the detectable label.

The enzyme or colloidal gold spheres are preferably conjugated to the secondary binding reagent (such as goat anti-human IgG or protein A).

For detection of the enzyme-conjugated reagent, a chromogenic substrate is used. For alkaline phosphatase, the chemical substrates, 5 bromo-4 chloro-3-indoyl phosphate (BCIP) and nitro-blue tetrazolium (NBT) are used. For horse radish peroxidase, 3,3'-diaminobenzidine (DAB), 4 chlorol-naphthol (4CN) and 3-amino-9-ethyl carbazole is used. One of skill in the art will readily determine which substrate to use.

The use of the colloidal gold spheres provides a one-step detection system as the gold provides a rose/red color and no further incubation steps are required. If virus-specific antibodies are present in the test sera, colored bands corresponding to the position of one or more of the viral antigens will be seen on the nitrocellulose strip.

In a preferred embodiment, goat anti-human IgG conjugated with alkaline phosphatase is used as the enzyme conjugated second reagent.

In another embodiment, the secondary reagent (such as the goat anti-human IgG antibody may be conjugated to a first enzyme which is "coupled" to a second system which results ultimately in generation and deposition of a chromophore where the antigen-antibody reaction occurred on the solid phase. Thus, for example, the conjugated first enzyme may act on a first substrate which yields a product which when coupled with a second enzyme substrate reaction, or with a second coupled dye (such as a diazo dye), yields a product which is detectable and reflects the presence of the first enzyme. The second substance may be a co-enzyme precursor plus a chromogenic precursor, wherein the first enzyme reacts with the co-enzyme precursor, such as, for example nicotin-amide adenine dinucleotide phosphate (NADP), under suitable conditions to produce NAD, which is then employed in a series of cyclic chemical reactions forming a generation catalyst which acts to produce a detectable product from a precursor (such as a chromogenic precursor). The generation catalyst can be another enzyme, e.g. diaphorase, as a reduction catalyst. The presence of a chromophore so generated can be visually detected or measured by colorimetric techniques known in the art. For example, a cyclic NAD/NADH reaction with different oxidation-reduction catalysts for phosphatase determination is disclosed in EPO Publication 0058539. In an additional example, the enzyme lactic dehydrogenase (LDH), in the presence of lactate, causes reduction of NAD to NADH, which can reduce a tetrazolium salt to a reduced formazan, which can be detected visually or colorimetrically at the appropriate wavelength. The amount of formazan formed is a measure of LDH activity. Chromophore precursors useful in this embodiment include tetrazolium salts such as 2-(p-iodophenyl),3-(p-nitrophenyl)-5-phenyltetrazolium chloride (INT); 3-(4,5-dimethylthiazol-2-yl)-2,5-diphenyl tetrazolium bromide (MTT); 2,2'5,5'-tetra-(p-nitrophenyl)-3,3'-(3,3'-dimethoxy-4,4'-diphenylene) diphenyltetrazolium chloride (TNBT); 2,2'-di(p-nitrophenyl)-5,5'-diphenyl-3,3'-(3,3'-dimethoxy-4,4'-diphenylene) diphenyl tetrazolium chloride (NBT); 2,2-diphenylene-3,3'5,5'-tetraphenyl ditetrazolium chloride (neotetrazolium chloride or NT); 2,3-5-triphenyltetrazolium chloride (TT); and the like.

Alternatively, alkaline phosphatase activity results in generation of NAD from NADP. The NAD can couple to the LDH reaction described above and result in similar formazan formation, which in this case would reflect the presence of alkaline phosphatase bound to the solid support.

As will be evident to one of skill in the art, the immunoassays and methods of the present invention can be used for improved detection of many types of viruses from any of a number of species. The invention is particularly useful for assay of retrovirus-specific antibodies in humans. However, it is also intended for other viruses, for example, retroviruses of other mammalian species such as simian retroviruses, feline retroviruses, and the like, and is therefore useful in veterinary as well as human medicine.

Having now generally described the invention, the same will be more readily understood through reference to the following examples which are provided by way of illustration, and are not intended to be limiting of the present invention, unless specified.

EXAMPLE 1

Immunoblot Capable of Distinguishing HIV-1 from HIV-2

Because of the extensive immunological cross-reactivity of HIV-1 and HIV-2, it is often not possible to distinguish an "indeterminate" HIV-1 immunoblot from a true HIV-2 seropositive sample. The immunoblot configuration described herein allows this distinction.

A. PREPARATION OF IMMUNOBLOT STRIPS

The polyacrylamide gel was polymerized between glass plates measuring 18 cm by 16 cm comprising of a 11% resolving lower gel and a 6% upper stacking gel. Approximately 60 µg of HIV-1 viral antigen lysate was mixed in a volume of 800 µl with sample buffer containing glycerol, 2-mercaptoethanol, and bromophenol blue and pyronin Y as tracking dyes. This mixture was layered onto the upper stacking gel and electrophoresed at 15 mA/gel, for the upper gel then at 25 mA/gel for the lower gel until the pyronin Y marker had migrated 10.5 cm into the lower gel. The gel was removed from the sandwiching glass plates, and the upper gel and 0.5 cm from the edge of the lower gel marker were trimmed off.

The proteins were then electrophoretically transferred onto nitrocellulose, using modifications of an established methodology (Towbin et al., supra). A piece of nitrocellulose measuring 12.8 cm by 10.5 cm, presoaked in a Tris-based buffer, was layered onto a piece of wet blotting paper, measuring 14 cm by 11.5 cm. The trimmed gel was gently layered onto the nitrocellulose paper. A uniform physical contact between the gel and nitrocellulose was maintained by removing excess air bubbles using a pair of smooth rollers. Another piece of wet blotting paper was placed on top, thereby sandwiching the gel. The blotting paper-gel-nitrocellulose-blotting paper sandwich was further sandwiched by 2 pieces of Scotch-Brite pads. This multi-layer preparation was placed within the transblot cell holder, immersed into the transblot tank with the nitrocellulose side of the sandwich directed toward the positive electrode (anode).

The proteins were transblotted by applying a voltage of 30V overnight (16 hours) followed by 100V for 1 hour. The nitrocellulose sheet was removed and kept moist in a tray containing a phosphate buffer.

Commercially available anti-human IgG was diluted, to a concentration of 10 µg/ml in 0.1M carbonate buffer, pH9.6. A genetically engineered HIV-1 envelope protein, at 7 µg/ml, and a HIV-2 specific synthetic peptide from the envelope sequence, at 15 µg/ml, all diluted in carbonate buffer, were applied to the transblotted nitrocellulose using a slotting apparatus. The anti-human IgG was slotted at approximately 1.6 cm from the lower end of the electrophoresed, transblotted protein zone, followed by the HIV-1 envelope protein at 1.3 cm and synthetic HIV-2 peptide at 1.0 cm respectively from the lower end. The lower end of the nitrocellulose is the area beyond which the lower molecular weight viral proteins had migrated. The protein solutions were removed by aspiration with a vacuum pump.

The nitrocellulose was removed from the slotting apparatus and blocked in PBS buffer containing 5% non-fat dry milk for 45 minutes at room temperature, (25° C.), on a rocker platform. The nitrocellulose was rinsed for 15 minutes at room temperature with PBS-Tween buffer. Nitrocellulose sheets were removed, air dried on paper towels, then left in a 37° C. oven for overnight drying. The sheet was cut into 3 mm or 4 mm wide strips and kept in dry containers till ready for the assay.

B. IMMUNOASSAY

Serum samples that had been previously identified as seropositive for HIV-1, seropositive for HIV-2 and indeterminate for HIV-1 with conventional immunoblot assays were assayed by incubation with the augmented western blot strips. These particular samples were selected for purposes of illustration. In normal use, an unknown serum sample from a patient would be tested. The strips were placed, right side up, onto each well of commercially available trays used for conventional HIV-1 western blot assays. The strips were prewetted by incubating in 2 ml each of a wash buffer (Tris-based, containing Tween 20 detergent). After 15–30 minutes, the buffer was aspirated, and 2 ml of blotting buffer, containing Tris, inactivated goat serum and 5% non fat dry milk were added. 20 µl of each test serum were added to each well containing buffer and nitrocellulose strip, and incubated overnight at room temperature on a rocker platform. The fluid was then removed by aspiration and the strips washed 3 times with 2 ml of wash buffer, with 5 minute soaks on the rocking platform between each wash. A commercially available anti-human IgG-alkaline phosphatase conjugate diluted with blotting buffer at recommended dilutions was added to the strips, incubated 30 minutes at room temperature and washed 3 times as described in the previous step. The viral bands were visualized after incubation of the strips with a commercially available solutions of nitroblue tetrazolium and 5 bromo-4-chloro-3 indolyl phosphate. Purplish-blue viral specific bands were observed indicating the presence of specific antibodies the test sera. The enzymatic reactions were stopped by rinsing the strips with distilled water.

C. RESULTS

Representative profiles of test sera are diagrammed in FIG. 2. Sera that contained specific anti-HIV-1 antibodies reacted with all natural viral proteins on the immunoblot strip, as well as the anti-human IgG band and the HIV-1 recombinant antigen band. A serum containing anti-HIV-2 antibodies tested on conventional HIV-1 immunoblot strips would normally react with HIV-1 proteins which are products of gag and pol genes, including p55, p24, p17, and p31, but would not react with HIV-1 specific env gene products. Such a reaction pattern would be classified as "indeterminate."

Using the augmented immunoblot strips, the HIV-2 sera reacted with the HIV-1 p24 and p31 bands, the anti-human IgG band (positive control) and the HIV-2 envelope-specific peptide band. This allowed immediate distinction of the HIV-2 seropositive sample from a HIV-1 seropositive sample.

EXAMPLE 2

The HIV-1 viral lysate profile could be further augmented by the direct application of synthetic viral proteins from other viruses such as HTLV-I.

HIV-1 viral lysate antigens were electrophoresed and transblotted as described in Example 1. The transblotted nitrocellulose was placed onto the slotting apparatus, and anti human IgG was slotted on to the nitrocellulose 1.6 cm from the lower end. A genetically-engineered HTLV-I envelope protein at 7 µg/ml was slotted into the next slot 1.3 cm from the lower end of the nitrocellulose. A HIV-1 positive serum from a patient co-infected with HTLV-I will react with the HIV-1 specific viral antigens as well as with the HTLV-I recombinant protein. An immunoblot strip formatted in this way allowed for the simultaneous serological distinction of HIV-1 infection and probable HTLV-I infection.

EXAMPLE 3

This augmented immunoblot format was further extended by using electrophoresed HTLV-I lysate antigens and HTLV-I recombinant antigens or synthetic peptides to augment the HTLV-I viral lysate profile. HTLV-I viral lysate generally comprised immunologically "weak" envelope glycoproteins, which result in weakly stained immunoblot profiles with HTLV-I seropositive serum.

To a standard HTLV-I viral lysate was added 3 µg/cm gel of a HTLV-I recombinant envelope protein, and the mixture was electrophoresed and transblotted as described in Example 1. Electrophoresis was performed on 12% polyacrylamide gels. The recombinant protein migrated as a band distinct from that of the other viral lysate proteins. The addition of the recombinant envelope protein therefore enhanced the detection of antibodies to the HTLV-I envelope proteins.

EXAMPLE 4

The immunoblot format as described in Example 3 is further configured to distinguish HTLV-I and HTLV-II specific infections. A HTLV-II specific recombinant protein is also added to the HTLV-I viral lysate for electrophoresis. Alternately, HTLV-I and HTLV-II synthetic proteins are applied in the slot format as in example 1 creating a configuration for the differentiation of HTLV-I from HTLV-II. An immunoassay performed as above using this format allows the detection of co-existing antibodies to HTLV-I and II.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for detecting HIV infection in a human blood sample, comprising
    adding the sample to a solid phase support having bound thereto (i) electrophoretically separated HIV-1 viral lysate proteins, (ii) an HIV-2-specific peptide antigen having the sequence LNSWGCAFRQVCHTTVPW, and (iii) a human immunoglobulin capture reagent;
    detecting the pattern of binding of serum antibodies in said sample to said HIV-1 proteins and to said HIV-2 antigen; and
    determining from said pattern, the presence in the serum sample of (i) HIV-1 infection, (ii) HIV-2 infection, (iii) lack of HIV infection, or (iv) indeterminate HIV-cross-reactivity.

2. The method of claim 1, wherein said human immunoglobulin capture reagent is anti-human immunoglobulin G (IgG) antibody.

3. The method of claim 1, which further includes, bound to the solid support, a synthetic HIV-1-specific viral envelope protein-derived antigen, said detecting of said pattern of binding further includes detection of binding to said HIV-1 specific antigen, and said determining further includes confirming the presence of HIV-1 infection in a weakly HIV-1 immunoreactive serum sample.

4. An immunoassay for detecting HIV infection in a human blood sample, comprising
    a solid phase support having bound thereto (i) electrophoretically separated HIV-1 viral lysate proteins, (ii) an HIV-2-specific peptide antigen having the sequence LNSWGCAFRQVCHTTVPW, and (iii) a human immunoglobulin capture reagent; and
    means for detecting the pattern of binding of serum antibodies in said sample to said HIV-1 proteins and to said HIV-2 antigen;
    wherein from said pattern, the presence in the serum sample of (i) HIV-1 infection, (ii) HIV-2 infection, (iii) lack of HIV infection, or (iv) indeterminate HIV-cross-reactivity is determined.

5. The immunoassay of claim 4, wherein said anti-human immunoglobulin capture reagent is anti-human immunoglobulin G (IgG) antibody.

6. The immunoassay of claim 4, which further includes, bound to the solid support, a synthetic HIV-1-specific viral envelope protein-derived antigen, said means for detecting means for detection of binding to said HIV-1 specific antigen, and from said pattern is further confirmed the presence of HIV-1 infection in a weakly HIV-1 immunoreactive serum sample.

* * * * *